(12) United States Patent
Kamble

(10) Patent No.: US 10,604,472 B2
(45) Date of Patent: Mar. 31, 2020

(54) AUTO-CATALYZED PROCESS FOR THE SYNTHESIS OF TRIBUTYL CITRATE (TBC)

(71) Applicant: COUNCIL OF SCIENTIFIC AND INDUSTRIAL RESEARCH, New Delhi, Delhi (IN)

(72) Inventor: Sanjay Pandurang Kamble, Pune (IN)

(73) Assignee: Council of Scientific & Industrial Research, New Delhi (IN)

( * ) Notice: Subject to any disclaimer, the term of this patent is extended or adjusted under 35 U.S.C. 154(b) by 0 days.

(21) Appl. No.: 15/777,148

(22) PCT Filed: Nov. 17, 2016

(86) PCT No.: PCT/IN2016/050406
§ 371 (c)(1),
(2) Date: May 17, 2018

(87) PCT Pub. No.: WO2017/085745
PCT Pub. Date: May 26, 2017

(65) Prior Publication Data
US 2018/0354886 A1 Dec. 13, 2018

(30) Foreign Application Priority Data
Nov. 17, 2015 (IN) .......................... 3744/DEL/2015

(51) Int. Cl.
*C07C 67/08* (2006.01)

(52) U.S. Cl.
CPC .................................. *C07C 67/08* (2013.01)

(58) Field of Classification Search
CPC ...................................................... C07C 67/08
USPC ......................................................... 560/180
See application file for complete search history.

(56) References Cited

U.S. PATENT DOCUMENTS 2,523,792 A 9/1950 Vahlteich et al.
2006/0252956 A1 11/2006 Miller et al.

FOREIGN PATENT DOCUMENTS

| CN | 104 478 716 A | | 4/2015 |
| CN | 104478716 | * | 4/2015 |
| CN | 104 892 418 A | | 9/2015 |
| WO | 03/008369 A1 | | 1/2003 |
| WO | WO-3008369 A1 | * | 1/2003 |

OTHER PUBLICATIONS

Aspi K. Kolah et al.; entitled "Reaction Kinetics of the Catalytic Esterification of Citric Acid with Ethanol"; Department of Chemical Engineering & Materials Science, Michigan State University; Ind, Eng. Chem. Res. 2007; No. 46; pp. 3180-3187.
Aspi K. Kolah et al.; entitled "Triethyl Citrate Synthesis by Reactive Distillation"; Department of Chemical Engineering & Materials Science, Michigan State University; Ind. Eng. Chem. Res. 2008; No. 47; pp. 1017-1025.

* cited by examiner

*Primary Examiner* — Deborah D Carr
(74) *Attorney, Agent, or Firm* — Baker & Hostetler LLP

(57) ABSTRACT

The present invention discloses a novel eco-friendly, cost effective, autocatalytic process for the synthesis of tributyl citrate (TBC) with high yields and purity.

13 Claims, 9 Drawing Sheets

AUTO-CATALYZED PROCESS FOR THE SYNTHESIS OF TRIBUTYL CITRATE (TBC)

CROSS-REFERENCE TO RELATED APPLICATIONS

This application is a National Stage of International patent application PCT/IN2016/050406, filed on Nov. 17, 2016, which claims priority to Indian patent application No. 3744/DEL/2015, filed on Nov. 17, 2015, the disclosures of which are incorporated by reference in their entirety.

FIELD OF THE INVENTION

The present invention relates to a process for the synthesis of tributyl citrate (TBC) with high yields and purity. More particularly, the present invention provides an eco-friendly, cost effective, auto-catalyzed process for the synthesis of tributyl citrate (TBC), wherein purity of tributyl citrate is in the range of 95 to 99.9%.

BACKGROUND AND PRIOR ART

Organic esters are important intermediates in chemical and pharmaceutical industries, and they are mostly produced by acid-catalyzed esterification reactions. The esters of bio-based organic acids fall into the category of benign or green solvents and are promising replacements for halogenated petroleum-based solvents in a wide variety of applications. Citric acid can be esterified with alcohols like ethanol and n-butanol through a series of reactions to yield tri-ethyl citrate (TEC) and tri-n-butyl citrate (TBC). TEC and TBC are used as nontoxic plasticizers in toys, medical products (e.g., as enteric coatings for controlled release drug delivery systems), printing ink coatings, cosmetics, and other applications. These plasticizers are also suitable as food additives such as whipping agents for dried egg whites, food flavorings, or food packaging materials. The global plasticizers market has been estimated at around 11 billion pounds per year; according to 2003 statistical data, the U.S. share of this market is 2.4 billion pounds.

TBC is widely used as a solvent and plasticizer in the field of food additives, food contact materials, medical products and cosmetics due to its high boiling point and lower molecular weight. At high temperatures TBC is a stable compound and act as biodegradable polymer. Since, TBC has been derived from the substances which are easily available from renewable resources by fermentation process; therefore TBC is an environmentally friendly plasticizer.

Industrially, TBC have been produced by the esterification reaction of citric acid with butanol with catalytic process. Traditionally, conc. sulphuric acid was used as catalyst. But catalytic esterification process becomes more complex due to increase of number of processes such as deacidification, neutralization, washing, drying, bleaching, and filtration process. Other than complexity, serious equipment corrosion, long reaction period large investment in equipment, poor reaction selectivity, low product quality, high-cost, colour depth, by-products makes more complex post-processing operations, wastewater capacity and serious environmental pollution. The cost of conc. sulphuric acid is low and having high catalytic activity as compared to the other catalyst used. Esterification of carboxylic acids with alcohols in presence of acid catalysts has been extensively investigated. Typical homogenous catalysts like $H_2SO_4$ and p-TSA are used but due to their miscibility with the reaction medium, however separation becomes a serious problem. In conventional manufacturing of tributyl citrate, various catalysts are used for esterification process. These include both homogeneous and heterogeneous catalysts. Major catalysts used are as are $H_2SO_4$, PTSA (para toluene sulphonic Acid), cation exchange resins, titanate, solid acid catalysts, ionic liquid catalysts etc.

Chinese patent application no. 104478716 discloses a process for the synthesis tributyl citrate plasticizer. The synthesis process comprises steps as follows: (1) an esterification reaction; (2) neutralization and washing; (3) distillation; (4) decolorization.

Chinese patent application no. 104892418 discloses a synthesis method for the preparation of acid tributyl citrate. The synthesis method comprises the following steps of stirring and reacting at the room temperature to obtain a product citric acid tributyl citrate by utilizing a condensing agent o-benzotriazole-N,N,N',N'-tetramethyluronium tetrafluoroborate (abbreviated as TATU) by means of esterification reaction of citric acid and n-butyl alcohol.

US patent application no. 20060252956 discloses a process for producing organic acid di- or tri-esters, particularly citric acid tri-esters, with the available acid groups esterified using countercurrent reactive distillation using acid catalysts in a structured packing. In the reactive distillation an organic acid di- or tri-ester is formed by chemical reaction and purified to its final state within the single column. Organic acid di- or tri-esters are produced at relatively low cost, with less waste production in by-products of the reaction, and in a less complicated manner than prior processes. Organic acid di- and tri-esters have uses as solvents, as plasticizers and in conversion products.

Article titled "Reaction kinetics of the catalytic esterification of citric acid with ethanol" by AK Kolah et al. published in *Ind. Eng. Chem. Res.*, 2007, 46 (10), pp 3180-3187 reports reaction kinetics for the reversible esterification reaction of citric acid with ethanol to form tri-ethyl citrate via mono-ethyl and di-ethyl citrates. The reaction was studied in batch isothermal experiments, self-catalyzed homogeneously by citric acid and the formed mono- and di-ethyl citrates, and heterogeneously catalyzed by macroporous Amberlyst-15 ion-exchange resin catalyst.

Article titled "Continuous process for esterification of citric acid: Formation of triethyl citrate" by Asthana et al. published in *ACS National Meeting Book of Abstracts*, 2007 reports a continuous process for the formation of triethyl citrate using cationic exchange resins as catalysts in a reactive distillation column and batch reactor. Vapor-liquid equilibrium studies for important binary mixtures have also been conducted. In a standard batch reaction, equilibrium was achieved after 16 hours; 99% of the citric acid was converted to a mixture of monoethyl, diethyl, and triethyl citrate, with a batch triethyl citrate selectivity of 64%. Kinetic parameters that include both ion-exchanged catalyzed reactions and self-catalyzed reactions were generated by non-linear regression of batch experimental data in MATLAB.

U.S. Pat. No. 2,523,792 discloses citric acid ester compositions, and more particularly to compositions including esters of citric acid. The monoisopropyl citrate is prepared by using Equal parts of U. S. P. citric acid and commercial 99% isopropyl alcohol are heated together under reflux, without catalyst for 118 hours at 92° C.

PCT application no. 2003008369 discloses a method for the production of citric acid esters of citric acid and monovalent straight or branched chain alcohols having a chain length of 4 to 10 carbon atoms. The process for the catalytic esterification of citric acid with straight or branched chain 4-10 carbon atoms with alcohols comprises three stages: a) in the first stage, the reaction mixture is heated to temperatures ranging from 100 to 130° C. and esterification takes place by means of auto-catalysis up to a conversion rate of 80 to 90%; b) in the second stage the catalyst is added, the reaction temperature is adjusted between 100 and 300° C. depending on the stability of the respective ester, and esterification continues up to a conversion rate of 90 to 95° C.; and c) in the third stage the reaction temperature is maintained at the highest value reached in the second stage, anhydrous alcohol is optionally added depending on the respective alcohol components, the supply of inert gas is multiplied by three or six relative to the first two sections.

Article titled "Triethyl citrate synthesis by reactive distillation" by AK Kolah et al. published *Ind. Eng. Chem. Res.*, 2008, 47 (4), pp 1017-1025 reports a continuous reactive distillation process is proposed for the synthesis of triethyl citrate from citric acid and ethanol in the presence of macroporous Amberlyst 15 ion-exchange resin catalyst.

Homogeneous catalysts offer a number of important advantages over their heterogeneous counterparts. For example, all catalytic sites are accessible because the catalyst is usually a dissolved metal complex. Furthermore, it is often possible to tune the chemo selectivity, region selectivity, and/or enantio selectivity of the catalyst. Despite these advantages, many homogeneous catalytic systems have not been commercialized because of one major disadvantage compared with heterogeneous catalysts the difficulty encountered when trying to separate the reaction product from the catalyst and reaction solvent. This problem arises because the most commonly used separation method, distillation, requires elevated temperatures unless the product is very volatile. Most homogeneous catalysts are thermally sensitive, usually decomposing below 150° C. Other conventional processes such as chromatography or extraction also lead to catalyst loss. However, catalyst separation is tedious process involving distillation & separation process. These processes might not give 100% recovery of the catalyst which increases cost of the process. Many times catalyst is highly soluble in water which causes water pollution.

The catalytic processes that are known in the prior art have following limitations i) separation of catalyst ($H_2SO_4$ and P-TSA) from reaction mixture and its reuse is difficult ii) many impurities was formed in the presence of catalyst ($H_2SO_4$ and p-TSA) iii) catalytic process gave yellowish and brownish colored TBC product.

Therefore, there is need to develop a cost effective, eco-friendly process for the synthesis of TBC with high purity and yield. Accordingly, the present inventors provide an eco-friendly, cost effective, autocatalytic process for the synthesis of tributyl citrate (TBC) with high yields and purity.

OBJECTIVE OF INVENTION

The main objective of the present invention is to provide an eco-friendly, cost effective, autocatalytic process for the synthesis of tributyl citrate (TBC) with high yields and purity.

SUMMARY OF THE INVENTION

Accordingly, the present invention provides an auto-catalyzed process for synthesis of tributyl citrate comprising the step of:

a) Adding citric acid solution in butanol to reactor followed by heating at temperature in the range of 100° C. to 150° C.;
b) Removing the sample of step (a) from reactor as initial sample and collecting the vapours of butanol and water in the separator via condenser;
c) Recycling the upper layer of butanol of step (b) to column followed by removal of water periodically to afford tributyl citrate;
   Wherein, purity of said tributyl citrate is in the range of 95 to 99.9%.

In a preferred embodiment, yield of tributyl citrate is in the range of 17% to 87%.

In another preferred embodiment, said butanol is n-butanol or iso-butanol.

In yet another preferred embodiment, mole ratio of citric acid to butanol is in the range of 1:3 to 1:6.

In still another preferred embodiment, said reaction is carried out for the period in the range of 1 to 10 hrs.

In yet still another preferred embodiment, colorless product is obtained.

In yet still another preferred embodiment, said process is carried out in semi-continuous mode of operation.

In yet still another preferred embodiment, said process is carried out in continuous mode of operation.

DETAILED DESCRIPTION OF THE INVENTION

The invention will now be described in detail in connection with certain preferred and optional embodiments, so that various aspects thereof may be more fully understood and appreciated.

In view of above, the present invention provides a novel eco-friendly, cost effective, autocatalytic process for the synthesis of TBC with high yields and purity.

In an embodiment, the present invention provides an auto-catalyzed process for synthesis of tributyl citrate comprising the step of:

a) Adding citric acid solution in butanol to reactor followed by heating at temperature in the range of 100° C. to 150° C.;

b) Removing the sample of step (a) from reactor as initial sample and collecting the vapours of butanol and water in the separator via condenser;
c) Recycling the upper layer of butanol of step (b) to column followed by removal of water periodically to afford tributyl citrate;
Wherein, purity of said tributyl citrate is in the range of 95 to 99.9%.

In a preferred embodiment, yield of tributyl citrate is in the range of 17% to 87%.

In another preferred embodiment, said butanol is n-butanol or iso-butanol.

In yet another preferred embodiment, mole ratio of citric acid to butanol is in the range of 1:3 to 1:6.

In still another preferred embodiment, said reaction is carried out for the period in the range of 1 to 10 hrs.

In yet still another preferred embodiment, colorless product is obtained.

In yet still another preferred embodiment, said process is carried out in semi-continuous mode of operation In yet still another preferred embodiment, said process is carried out in continuous mode.

Figure 7:
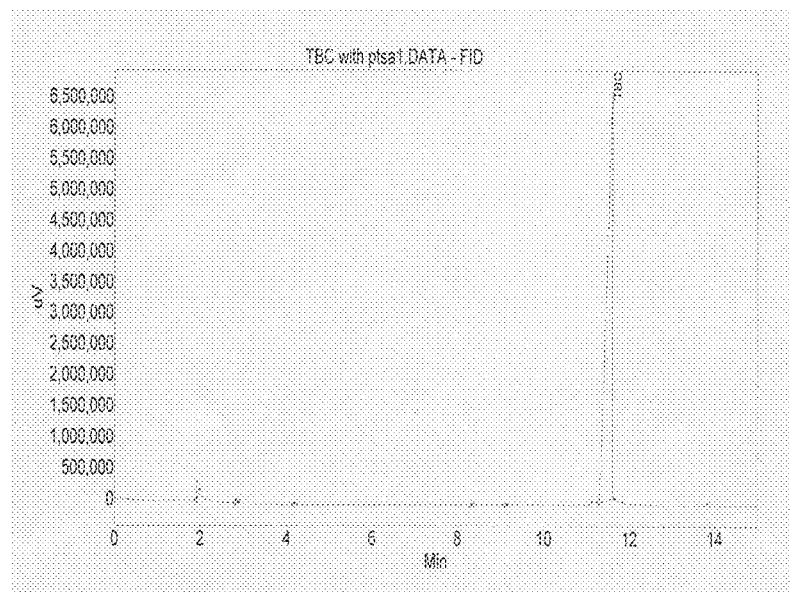
FIG. 7: depicts GC chromatogram for PTSA catalyst.
Figure 8:
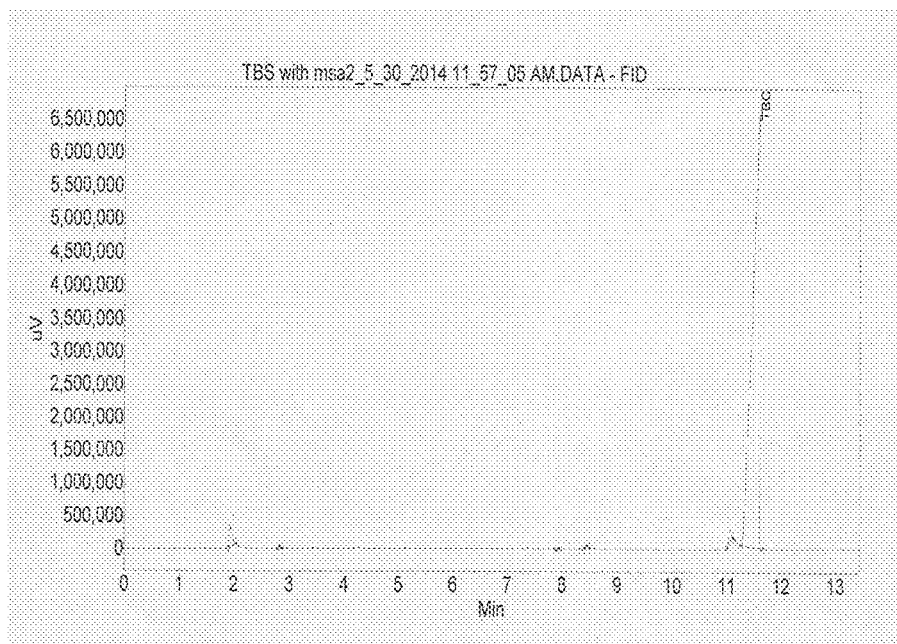
FIG. 8: depicts GC chromatogram for MSA catalyst.
Figure 9:
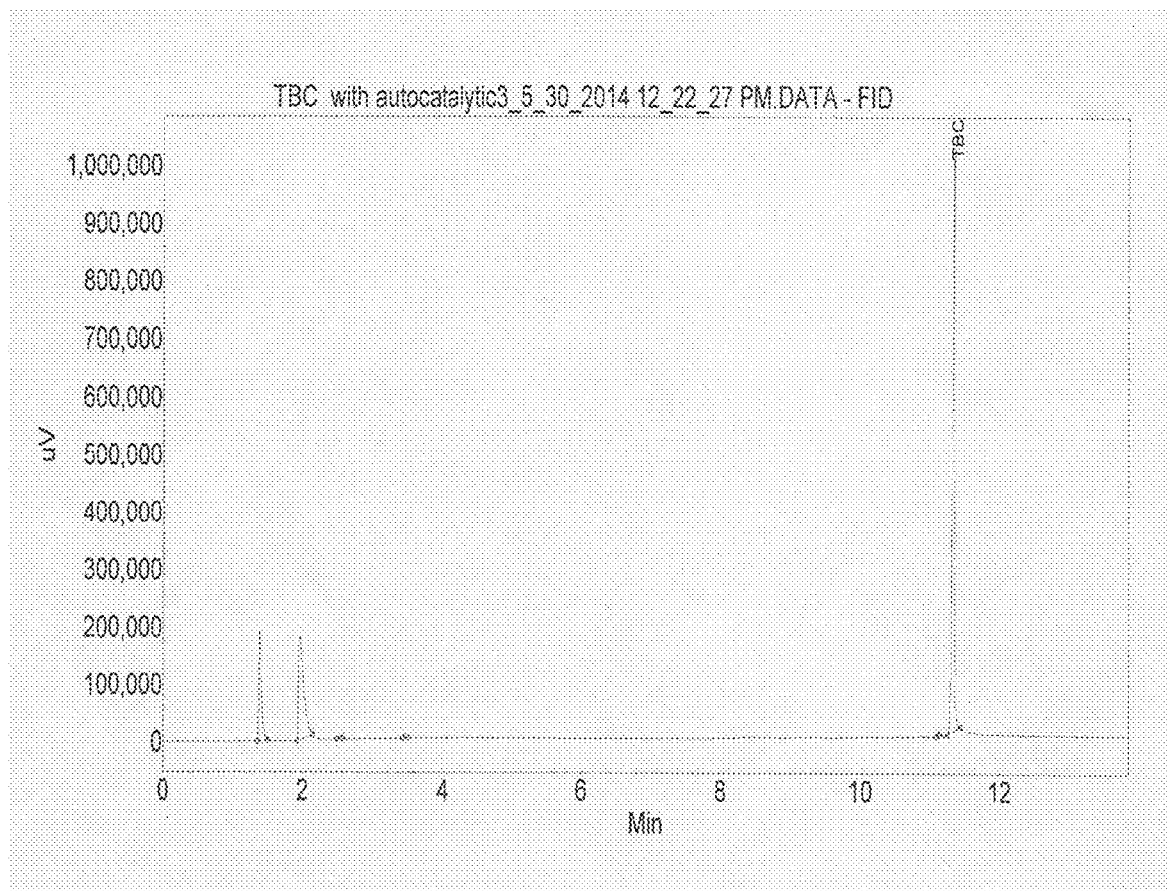
FIG. 9: depicts GC chromatogram for auto-catalyst.

The auto-catalyzed process for synthesis of tributyl citrate is as shown below in Scheme 1 and Scheme 2:

where as in the chromatogram of the auto-catalytic reaction product, apart from tri ester small amount of mono, di has been observed as shown in FIG. 7-9. By using GC calibration the purity of the TBC is calculated as shown in the Table 5.

TABLE 5

Purities of TBC sample using homogenous catalyzed reaction and autocatalytic reaction

| Catalysts | Area of TBC in GC (uV/min) | Purity (%) |
|---|---|---|
| PTSA | 594132.5 (dark yellow color) | 98.2 |
| MSA | 604159.4 (dark yellow color) | Exceeds 99.8 |
| Auto-catalytic | 611735.2 (colorless sample) | Exceeds 99.9 |

The TBC sample of homogeneous catalyzed reaction and autocatalytic reaction is analyzed in UV-spectrometer for its purity. Acetonitrile is used as the solvent for reference cell in UV-spectrometer. The absorbance of UV rays (200-400 nm) at different concentrations samples are provided in the Table 6. The Table 6 shows that absorbance of UV for autocatalytic reaction sample is much greater than the product obtained by homogeneous catalytic reaction. It indicates Scheme: 1

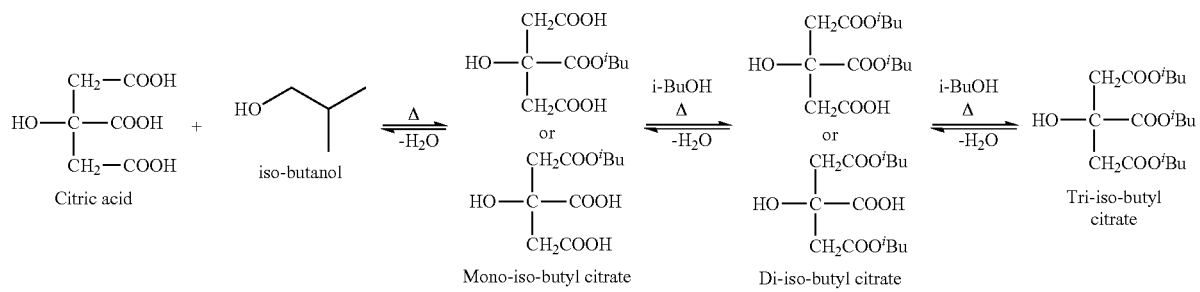

Scheme: 2

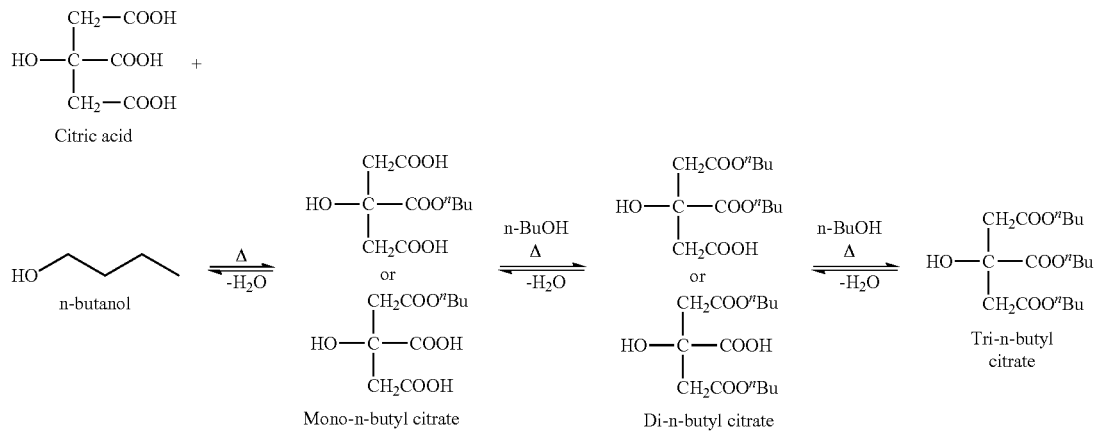

In an aspect, the present invention provides a process for the synthesis of TBC in the laboratory scale as well as pilot scale using reactive distillation column via autocatalytic approach.

Figure 5:
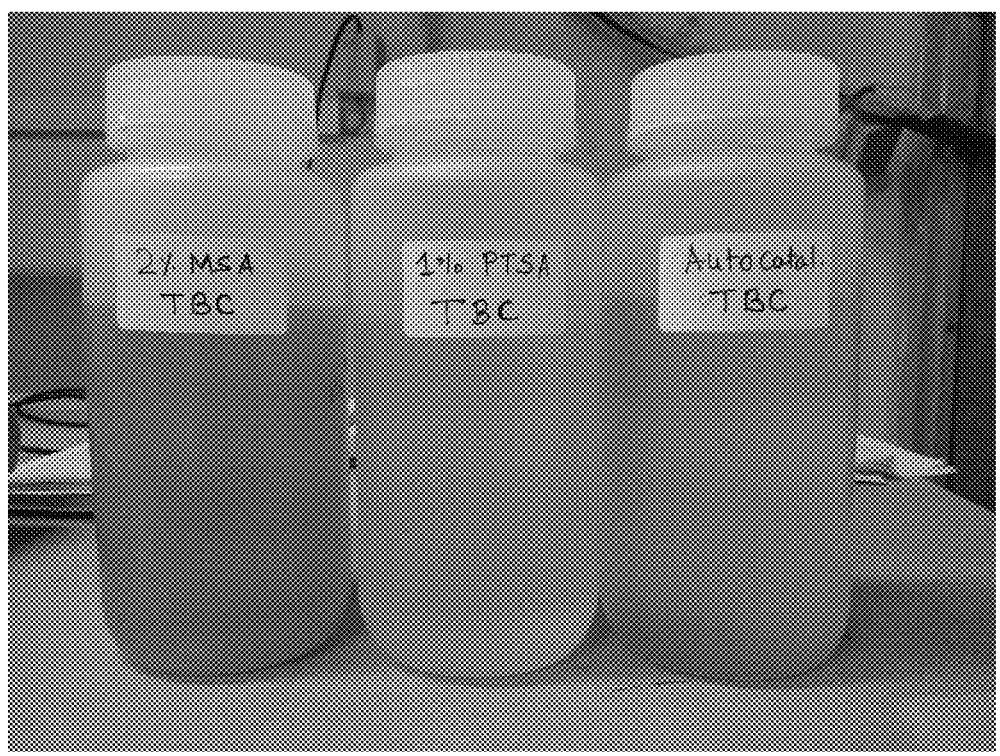
FIG. 5: depicts photograph of TBC samples prepared by autocatalytic and catalytic methods.

In the chromatogram of homogeneous catalyzed reaction product, some small quantities of impurities are observed that auto-catalytic reaction product has no impurity and also colorless solution is achieved in autocatalytic reaction than the homogeneous catalytic reaction sample (FIG. 5).

Figure 10:
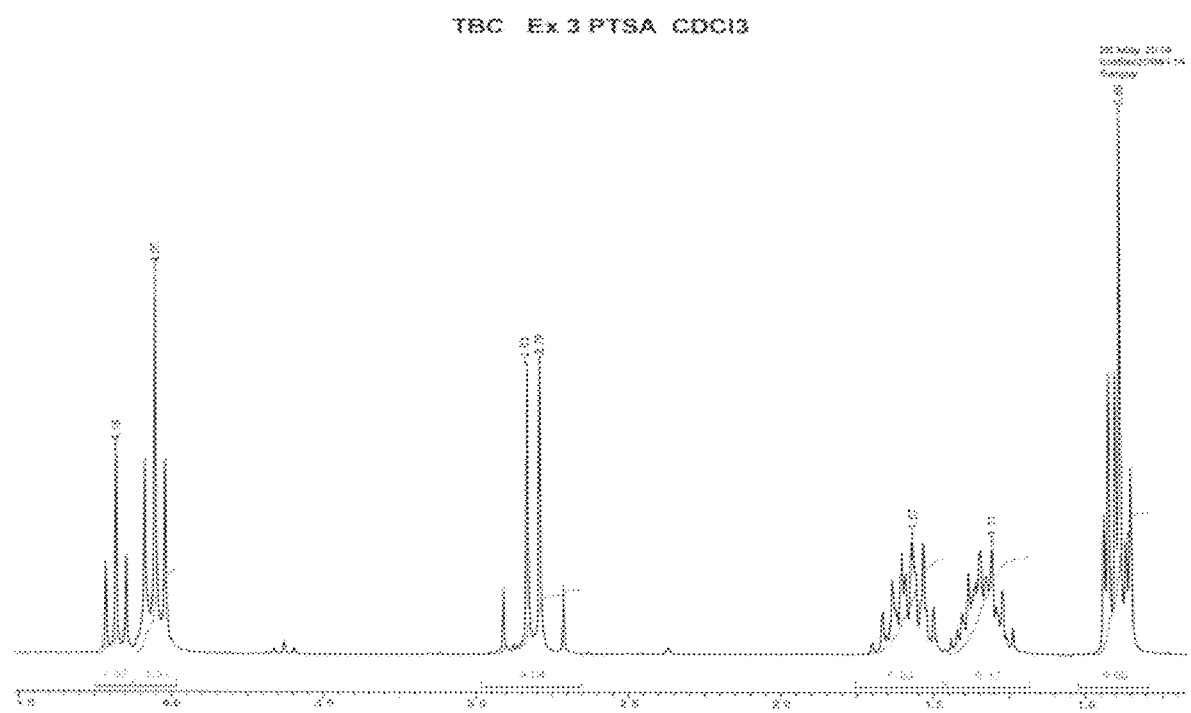
FIG. 10: depicts NMR graph for TBC (PTSA catalyst).
Figure 11:
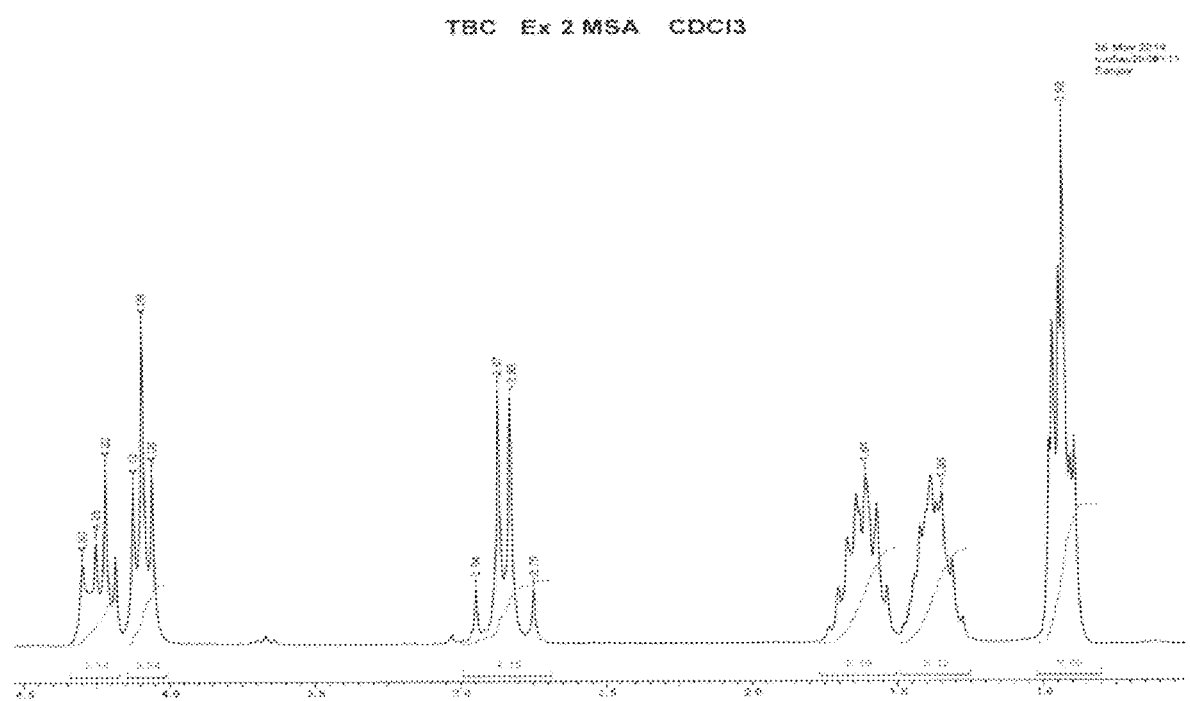
FIG. 11: depicts NMR graph for TBC (MSA catalyst).
Figure 12:
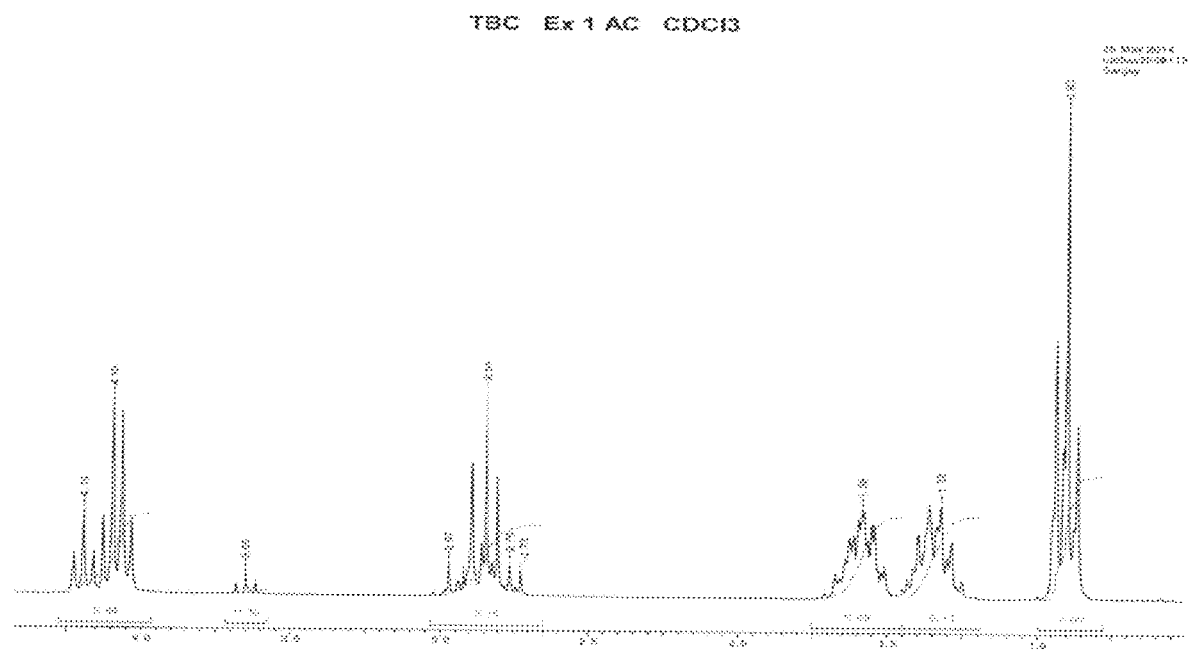
FIG. 12: depicts NMR graph for TBC (autocatalyst).

The NMR graphs confirm the formation of structure of TBC in the reaction mixture. The graphs provides different types of protons present in the structure as well as number of methyl groups with types of bonds as shown in FIG. 10-12. The calculations for TBC structure are provided in the Table 7.

The following examples, which include preferred embodiments, will serve to illustrate the practice of this invention, it being understood that the particulars shown are by way of example and for purpose of illustrative discussion of preferred embodiments of the invention.

EXAMPLES

Example 1

Figure 1:
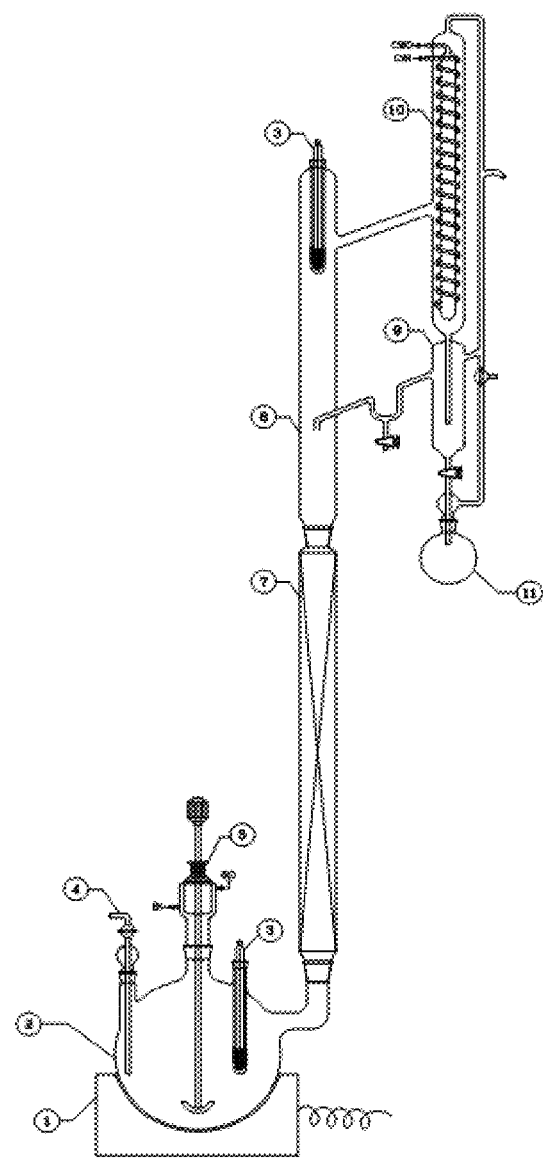
FIG. 1: depicts reactive distillation assembly for esterification of citric acid. 1: Heating mentle, 2: Reactor/Distillation still, 3: Thermowell/Thermameter, 4: Sampling point, 5: Stuffing box, 6: Motor, 7: Column, 8: Distillation head, 9: Phase separator, 10: Condenser, 11: Aqueous phase receiver

The experimental setup for reaction distillation of citric acid was shown in FIG. 1. The experimental set up consists of reboiler, column, condenser and liquid separator. The volume of reactor (reboiler) is 1 L. Three necks were used for connecting glass column having length 0.4 m, inserting the temperature indicator and deep tube for taking sample with regular interval of time respectively. The column was packed with radom packing (glass rings). The experimental setup for batch mode was designed to see the influence of various operating reaction parameters.

A. Procedure for Synthesis of TBC:

In a typical reaction the citric acid (193 gm) saturated solution in n-butanol (297 gm) was added to reactor which was heated at temperature ranging from 100 to 150° C. via oil bath heater. Once the expected reaction temperature is reached then a sample was withdrawn from the reboiler as initial sample. The column top end was connected to condenser and chilling water supplied to condenser in order to maintain temperature around 25° C. The vapor of butanol and water are collected in the separator via condenser, where upper layer of butanol was again recycled to column. The water was periodically removed from the separator at the same time samples were taken from the reboiler and analyzed for its content.

B. Downstream Processing of Reaction Mixture for Purification of TBC:

After reaction the mixture is subjected to rotary evaporator for purification of TBC from butanol, citric acid or catalyst. The separation was carried under vacuum. After separating TBC product on rotary evaporator, sample was analyzed for its purity by using GC, UV spectrophotometer, GCMS and NMR.

Figure 2:
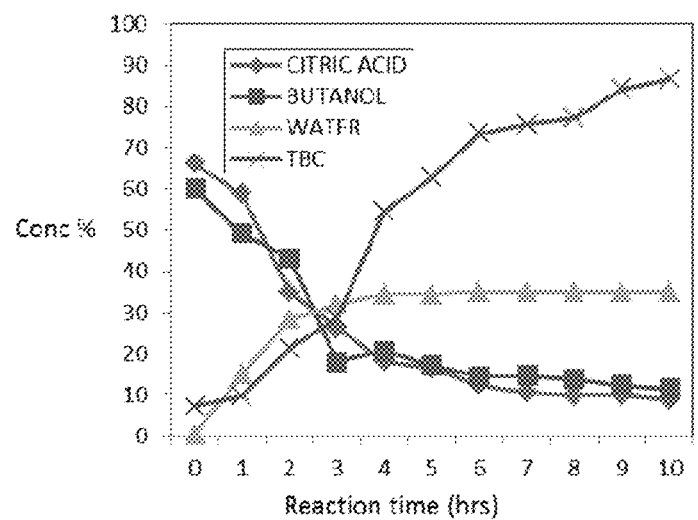
FIG. 2: depicts conc. profile of reactant and product for experiment number 5.
Figure 3:
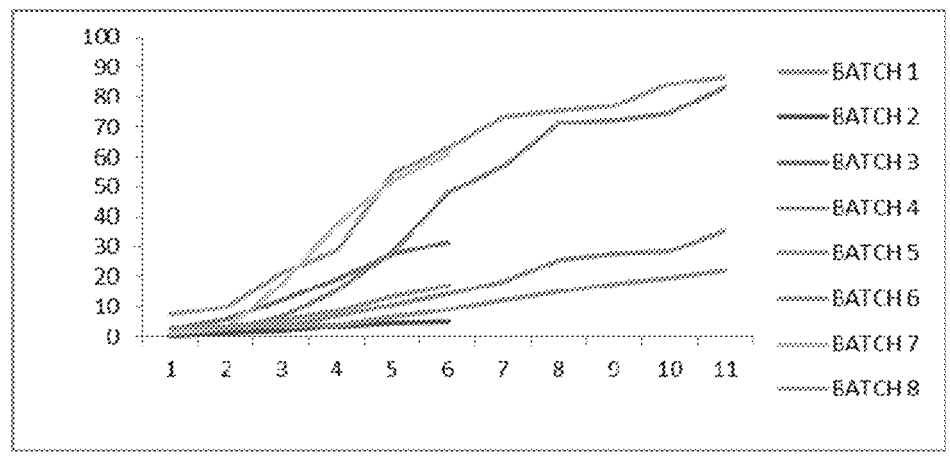
FIG. 3: depicts % TBC formation for different 8 experiments.

Example 2: Optimization of Process Parameters for Esterification of Citric Acid Experimental design for esterification of citric acid to tributyl citrate was carried out with a help of Plackett Burman Deign. Though various experimental design models are available, Plackett Burman design eliminates the need of large number of experiments as compared to other models. Plackett-Burman experimental design is used to identify the most important factors early in the experimentation phase when complete knowledge about the system is usually unavailable. The seven variables and eight experiments Plackett-Burman design the experiments (DOE) model was selected for optimization of the operating parameters for esterification of citric acid. The design of experiments (DOE) is a useful tool for identification of operating parameters that affect the reaction and it also helps in reducing the number of experiments to be carried out to achieve optimization condition. The speed of agitation (A), molar ratio (B), reaction temperature (C) and reaction time (D) were selected as the main operating parameters and the remaining three variables are dummy variables (E, F and G) which are used to determine experimental error. The low and high values were assigned to the main operating parameters on the basis of previous experimental knowledge. The high and low values of these operating parameters are shown in Table 1. The Plackett-Burman DOE model is presented in the Table 2. FIG. 2 shows conc. profile of reactant and product during the course of reaction for experiment number 5. While FIG. 3 shows % TBC formation for different experiments (Batch 1 to 8).

TABLE 1

Parameter Range for Design of Experiments

| Parameter | High Value (1) | Low Value (−1) |
|---|---|---|
| RPM | 500 | 300 |
| Molar Ratio | 1:06 | 1:04 |
| Temperature (° C.) | 150 | 120 |
| Time (hr) | 10 | 5 |

TABLE 2

Plackett-Burman design of experiments model for seven factors and eight experiments

| Number of Run | A | B | C | D | E | F | G |
|---|---|---|---|---|---|---|---|
| 1 | 1 | 1 | 1 | −1 | 1 | −1 | −1 |
| 2 | −1 | 1 | 1 | 1 | −1 | 1 | −1 |
| 3 | −1 | −1 | 1 | 1 | 1 | −1 | 1 |
| 4 | 1 | −1 | −1 | 1 | 1 | 1 | −1 |
| 5 | −1 | 1 | −1 | −1 | 1 | 1 | 1 |
| 6 | 1 | −1 | 1 | −1 | −1 | 1 | 1 |
| 7 | 1 | 1 | −1 | 1 | −1 | −1 | 1 |
| 8 | −1 | −1 | −1 | −1 | −1 | −1 | −1 |

A: speed of agitation (rpm), B: molar ratio (Citric Acid: n-butanol), C: reaction temperature (° C.) and D: reaction time (hrs); E, F and G are dummy variables.

The effect of various operating parameter on the yield of tributyl citrate was established by using Plackett-Burman model. For finding the effect of A, calculation of the sum of the conversion in those batches where value of A is high is performed. Similar exercise is performed where value of A is low. Then the difference of these sums is divided by half the number of experiments, i.e., 4. The effect of each parameter is shown in Table 3. It is clear from the results that speed of agitation does not affect conversion as its effect is less than the experimental error. This was expected because the reaction is auto-catalyzed. From DOE results (Table 3), it was found that the temperature (C) and reaction time (D) are the most significant parameters that affect the formation of tributyl citrate.

TABLE 3

Effect of individual parameter using design of experiments (DOE)

| Run Number | (A) Speed agitation (RPM) | (B) Molar Ratio | (C) Temp (°C.) | (D) Time (hr) | (E) A | (F) B | (G) C | % Conversion |
|---|---|---|---|---|---|---|---|---|
| 1 | 1 | −1 | −1 | 1 | −1 | 1 | 1 | 85.7 |
| 2 | 1 | 1 | −1 | −1 | 1 | −1 | 1 | 42.37 |
| 3 | 1 | 1 | 1 | −1 | −1 | 1 | −1 | 78.01 |
| 4 | −1 | 1 | 1 | 1 | −1 | −1 | 1 | 85.49 |
| 5 | 1 | −1 | 1 | 1 | 1 | −1 | −1 | 86.58 |
| 6 | −1 | 1 | −1 | 1 | 1 | 1 | −1 | 65.69 |
| 7 | −1 | −1 | 1 | −1 | 1 | 1 | 1 | 77.54 |
| 8 | −1 | −1 | −1 | −1 | −1 | −1 | −1 | 49.56 |
| Conversion effects | 3.59 | −6.96 | 21.07 | 18.99 | −6.6 | 10.74 | 2.81 | |

Figure 6:
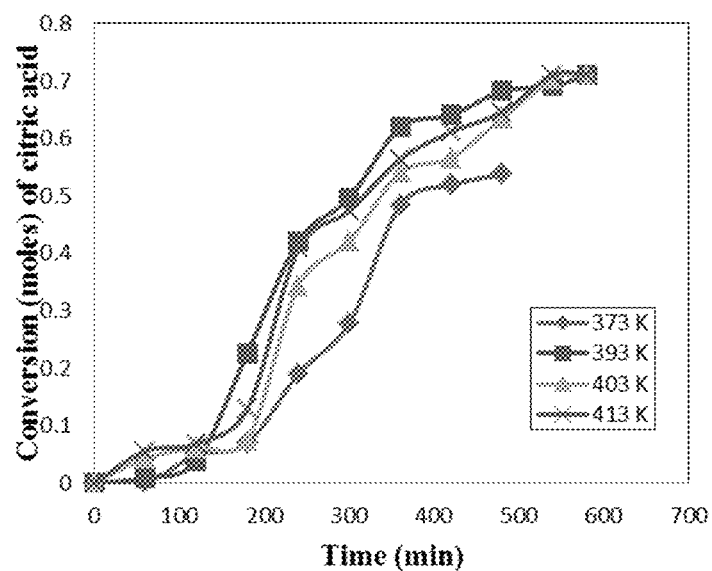
FIG. 6: depicts effect of temperature on conversion of citric acid.

The effect of temperature on the esterification reaction of citric acid with butanol has been studied by varying the temperature in the range of 373 K-413K. The conversion of citric acid with time for auto-catalyzed reaction at different temperatures is shown in FIG. 6. The conversion of citric acid increases with the increase in temperature because increase in temperature increases the number of molecules with high energy which provides greater activation energy to reaction. However, with increases in temperature the colour of TBC sample slightly becomes yellowish, hence 403 K was chosen as optimum temperature for synthesis of TBC.

After carrying out these set of experiments, it was observed that experiment #5 gives maximum conversion of citric acid about 87% whereas the experiment number 2 gives least conversion of 42%. From Table 3, it is observed that reaction time and reaction temperature are dominant factors influencing rate of reaction most whereas molar ratio and stirrer speed are insignificant factors. Hence, optimum reaction parameters were chosen for further experiments.

The effect of temperature was found to be a factor of 21.07 and the positive value suggests that the higher conversion will be obtained at a higher temperature. It is also evident from Table 4 that the higher formation of tributyl citrate occurs at higher reaction time. The effect of reaction time was found to be 18.99 suggesting that higher conversion will be obtained over a period of time, whereas the molar ratio and speed of agitation has negligible effect on the formation of tributyl citrate.

Figure 4:
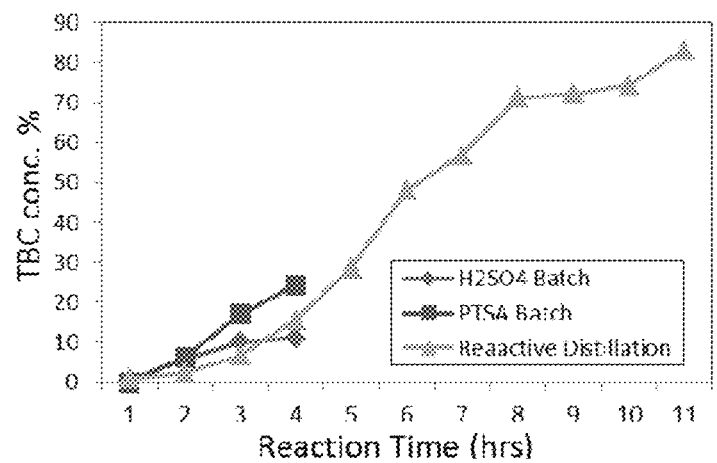
FIG. 4: depicts % shows formation of TBC in presence of $H_2SO_4$, PTSA catalyst in batch mode operation and autocatalyst approach in reactive distillation mode of operation.

Example 3: Comparison of TBC Formation Using Auto-Catalyst, $H_2SO_4$ and PTSA Catalyst The esterification of citric acid was also performed in presence $H_2SO_4$ and PTSA catalyst as well as absence of catalyst in batch mode of operation. FIG. 4 shows % formation of TBC in presence of $H_2SO_4$, PTSA catalyst in batch mode operation and auto-catalyst approach in reactive distillation mode of operation. It can be seen that only 11% and 24% of TBC were formed in the presence of $H_2SO_4$, and PTSA catalyst at reaction time of 3 hours respectively. Whereas reactive distillation approaches using auto-catalyst gives around 83% TBC at reaction time of 10 hrs. The major advantage of autocatalytic process is highly pure, colourless TBC is produced whereas catalytic ($H_2SO_4$ and PTSA) process as following limitations i) separation of catalyst ($H_2SO_4$ and PTSA) from reaction mixture and its reuse is difficult ii) many impurities were formed in the presence of catalyst ($H_2SO_4$ and PTSA) as compared to auto-catalyst process iii) catalytic process gave yellowish and brownish colour to the product whereas autocatalytic RD approach gives colorless TBC product. FIG. 5 shows the actual photographs of TBC samples prepared by catalytic and autocatalytic methods.

Example 4: Characterization

Samples were taken periodically from the reactor in order to find out concentration of TBC and unreacted citric acid. The reaction mixture sample was analyzed by gas chromatography (Broker GC 430 Model) in order to measure the

TABLE: 4

The % formation of TBC in different 8 experiments
% formation of TBC in different 8 EXPTS

| SR NO | TIME (HRS) | EXPT1 | EXPT2 | EXPT3 | EXPT4 | EXPT5 | EXPT6 | EXPT7 | EXPT8 |
|---|---|---|---|---|---|---|---|---|---|
| 1 | 0 | 0.00 | 0.00 | 2.70 | 1.01 | 7.24 | 2.77 | 0.95 | 2.90 |
| 2 | 1 | 1.15 | 0.92 | 5.68 | 2.30 | 9.69 | 3.25 | 2.98 | 3.33 |
| 3 | 2 | 3.36 | 1.64 | 12.37 | 6.73 | 21.31 | 4.03 | 17.66 | 5.37 |
| 4 | 3 | 6.93 | 3.53 | 19.03 | 15.66 | 28.73 | 4.00 | 37.52 | 8.55 |
| 5 | 4 | 10.66 | 4.76 | 27.42 | 28.56 | 54.38 | 6.60 | 52.08 | 13.45 |
| 6 | 5 | 14.44 | 5.11 | 31.52 | 48.06 | 62.86 | 8.94 | 61.11 | 17.20 |
| 7 | 6 | 18.17 | — | — | 57.03 | 73.40 | 12.31 | — | — |
| 8 | 7 | 25.56 | — | — | 71.32 | 75.62 | 14.89 | — | — |
| 9 | 8 | 27.45 | — | — | 72.24 | 77.21 | 17.58 | — | — |
| 10 | 9 | 28.54 | — | — | 74.50 | 84.25 | 19.58 | — | — |
| 11 | 10 | 35.28 | — | — | 83.27 | 86.62 | 21.87 | — | — | concentration of TBC. The HP 5 column was used for the analysis of reaction mixture. The temperature of injector and detector was kept at 300° C. and FID detector was used employed for analysis of reaction mixture. The analysis was performed in the presence of H$_2$ as carrier gas. The column temperature was varied from 50° C. to 280° C. with ramp rate of 20° C./min. The colour and purity of TBC was analysed by UV spectrometer and GC-MS, NMR method respectively. The reaction sample was titrated with KOH in order to calculate the quantity of unreacted citric acid.

a) Analysis of TBC Sample by Gas Chromatography (GC):

In the chromatogram of homogeneous catalyzed reaction product, some small quantities of impurities are observed whereas in the chromatogram of the auto-catalytic reaction product, apart from tri ester small amount of mono, di has been observed as shown in FIG. 7-9. By using GC calibration the purity of the TBC was calculated as shown in the Table 5.

TABLE 5

Purities of TBC sample using homogenous catalyzed reaction and autocatalytic reaction

| Catalysts | Area of TBC in GC (uV/min) | Purity (%) |
|---|---|---|
| PTSA | 594132.5 (dark yellow color) | 98.2 |
| MSA | 604159.4 (dark yellow color) | Exceeds 99.8 |
| Auto-catalytic | 611735.2 (colorless sample) | Exceeds 99.9 | b) Analysis of TBC Sample by UV-Spectrometer:

The TBC sample of homogeneous catalyzed reaction and autocatalytic reaction was analyzed in UV-spectrometer for its purity. Acetonitrile was used as the solvent for reference cell in UV-spectrometer. The absorbance of UV rays (200-400 nm) at different concentrations samples are provided in the Table 6. The Table 6 shows that absorbance of UV for autocatalytic reaction sample was much greater than the product obtained by homogeneous catalytic reaction. It indicates that auto-catalytic reaction product has no impurity and also colorless solution is achieved in autocatalytic reaction than the homogeneous catalytic reaction sample (FIG. 5).

TABLE 6

Absorbance at different TBC samples prepared by catalytic and autocatalytic method

| Sr. No. | Catalysts | $\lambda_{max}$ (nm) | Concentration (ppm) | Absorption |
|---|---|---|---|---|
| 1. | p-TSA | 289 | 5 | 0.218 |
|  |  |  | 10 | 0.240 |
| 2. | MSA | 289 | 5 | 0.194 |
|  |  |  | 10 | 0.236 |
| 3. | Autocatalyst | 289 | 5 | 0.275 |
|  |  |  | 10 | 0.310 |
| 4. | Authentic TBC sample | 289 | 5 | 0.221 |
|  |  |  | 10 | 0.285 | c) Analysis of TBC Sample by Nuclear Magnetic Resonance (NMR):

The NMR graphs confirm the formation of structure of TBC in the reaction mixture. The graphs provides different types of protons present in the structure as well as number of methyl groups with types of bonds as shown in FIG. 10-12. The calculations for TBC structure are provided in the Table 7.

TABLE 7

Number of protons and methyl groups with types of bonds

| Sr. No. | Types of proton | No. of protons | Methyl group with type of bond | No. of methyl groups |
|---|---|---|---|---|
| 1. | δ4.1 (t) | 6 | =CH$_2$ | 3 |
| 2. | δ2.84 (s) | 4 | =CH$_2$ | 2 |
| 3. | δ1.38 (m) | 6 | =CH$_2$ | 3 |
| 4. | δ1.32 (m) | 6 | =CH$_2$ | 3 |
| 5. | δ0.9 (t) | 12 | —CH$_3$ | 3 |

ADVANTAGES OF THE INVENTION

1. Green process, water is the only discharge and auto-catalyzed process, colorless product is obtained.
2. The process is scalable and is cheaper.
3. Commercially tributyl citrate is Rs.125/kg, but according to the disclosed process, cost is about Rs.90/kg.
4. Absence of separation step and no need of catalyst recovery & recycling.

The invention claimed is:

1. An auto-catalyzed process for synthesizing tributyl citrate comprising the steps of:
   a) heating a citric acid solution in butanol to a temperature in the range of 100° C. to 150° C. for 5 to 10 hours in a reactor to provide a sample;
   b) removing the sample of step (a) from the reactor and collecting the vapours of said butanol and water in a separator via a condenser; and
   c) recycling the upper layer of said butanol of step (b) to a column, followed by periodically removing said water to afford said tributyl citrate;
   wherein:
   the purity of said tributyl citrate is in the range of 95 to 99.9% and said tributyl citrate is colorless; and
   the process is performed in the absence of a catalyst, a neutralizing step, or a decolorizing step.

2. The process of claim 1, wherein the yield of said tributyl citrate is in the range of 17 to 87%.

3. The process of claim 1, wherein said butanol is n-butanol or iso-butanol.

4. The process of claim 1, wherein a mole ratio of said citric acid to butanol is in the range of 1:3 to 1:6.

5. The process of claim 1, wherein said process is carried out in semi-continuous mode of operation.

6. The process of claim 1, wherein said process is carried out in continuous mode of operation.

7. The process of claim 1, wherein the temperature is 120 to 150° C.

8. The process of claim 7, wherein the temperature is 120 to 140° C.

9. The process of claim 8, wherein the temperature is 130° C.

10. The process of claim 1, wherein the heating is performed for 6 to 10 hours.

11. The process of claim 1, wherein the heating is performed for 7 to 10 hours.

12. The process of claim 1, wherein the heating is performed for 8 to 10 hours.

13. The process of claim 1, wherein the heating is performed for 9 to 10 hours.

* * * * *